US00PP29248P2

(12) United States Plant Patent
Andersen

(10) Patent No.: US PP29,248 P2
(45) Date of Patent: Apr. 17, 2018

(54) ***SCHLUMBERGERA* PLANT NAMED 'THORSOPHIA'**

(50) Latin Name: *Schlumbergera hybrida*
Varietal Denomination: Thorsophia

(71) Applicant: Jorgen K. Andersen, Odense (DK)

(72) Inventor: Jorgen K. Andersen, Odense (DK)

(73) Assignee: Gartneriet Thoruplund A/S, Odense (DK)

( * ) Notice: Subject to any disclaimer, the term of this patent is extended or adjusted under 35 U.S.C. 154(b) by 0 days.

(21) Appl. No.: 15/330,640

(22) Filed: Oct. 22, 2016

(51) Int. Cl.
*A01H 5/02* (2006.01)

(52) U.S. Cl.
USPC ..... Plt./372

(58) Field of Classification Search
USPC ..... Plt./372
See application file for complete search history.

*Primary Examiner* — Susan McCormick Ewoldt
(74) *Attorney, Agent, or Firm* — C. A. Whealy

(57) ABSTRACT

A new and distinct cultivar of *Schlumbergera* plant named 'Thorsophia', characterized by its upright to broadly spreading plant habit; moderately vigorous growth habit; freely branching habit; dark green-colored leaves; freely flowering habit; and yellow-colored flower buds and flowers.

2 Drawing Sheets

Botanical designation: *Schlumbergera hybrida.*
Cultivar denomination: 'THORSOPHIA'.

BACKGROUND OF THE INVENTION

The present invention relates to a new and distinct cultivar of *Schlumbergera* plant, botanically known as *Schlumbergera hybrida* and hereinafter referred to by the name 'Thorsophia'.

The new *Schlumbergera* plant is a product of a planned breeding program conducted by the Inventor in Odense, Denmark. The objective of the breeding program is to create new strong and freely branching *Schlumbergera* plants with attractive flower color.

The new *Schlumbergera* plant originated from a cross-pollination conducted by the Inventor in Odense, Denmark in November, 2010 of a proprietary selection of *Schlumbergera hybrida* identified as code number 2010-7, not patented, as the female, or seed parent with a proprietary selection of *Schlumbergera hybrida* identified as code number 2010-3, not patented, as the male, or pollen, parent. The new *Schlumbergera* plant was discovered and selected by the Inventor as a single flowering plant from within the progeny of the stated cross-pollination in a controlled greenhouse environment in Odense, Denmark in November, 2012.

Asexual reproduction of the new *Schlumbergera* plant by cuttings in a controlled greenhouse environment in Odense, Denmark, since December, 2012 has shown that the unique features of this new *Schlumbergera* plant are stable and reproduced true to type in successive generations.

SUMMARY OF THE INVENTION

Plants of the new *Schlumbergera* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Thorsophia'. These characteristics in combination distinguish 'Thorsophia' as a new and distinct *Schlumbergera* plant:

1. Upright to broadly spreading plant habit.
2. Moderately vigorous growth habit.
3. Freely branching habit.
4. Dark green-colored leaves.
5. Freely flowering habit.
6. Yellow-colored flower buds and flowers.

Plants of the new *Schlumbergera* can be compared to plants of the female parent selection. Plants of the new *Schlumbergera* differ primarily from plants of the female parent selection in the following characteristics:

1. Plants of the new *Schlumbergera* are more freely branching than plants of the female parent selection.
2. Plants of the new *Schlumbergera* have darker green-colored leaves than plants of the female parent selection.
3. Plants of the new *Schlumbergera* and the female parent selection differ in flower color as plants of the female parent selection have red-colored flowers.

Plants of the new *Schlumbergera* can be compared to plants of the male parent selection. Plants of the new *Schlumbergera* differ primarily from plants of the male parent selection in the following characteristics:

1. Plants of the new *Schlumbergera* are more freely branching than plants of the male parent selection.
2. Plants of the new *Schlumbergera* and the male parent selection differ in flower color as plants of the male parent selection have orange-colored flowers.

Plants of the new *Schlumbergera* can be compared to plants of *Schlumbergera* 'Outono Brazil', not patented. In side-by-side comparisons, plants of the new *Schlumbergera* differ primarily from plants of 'Outono Brazil' in the following characteristics:

1. Plants of the new *Schlumbergera* are more compact than and not as vigorous as plants of 'Outono Brazil'.
2. Plants of the new *Schlumbergera* are more freely branching than plants of 'Outono Brazil'.

3. Plants of the new *Schlumbergera* have more rounded leaves than plants of 'Outono Brazil'.
4. Plants of the new *Schlumbergera* and 'Outono Brazil' differ in flower color as plants of 'Outono Brazil' have pale yellow-colored flowers.

BRIEF DESCRIPTION OF THE PHOTOGRAPHS

The accompanying colored photographs illustrate the overall appearance of the new *Schlumbergera* plant showing the colors as true as it is reasonably possible to obtain in colored reproductions of this type. Colors in the photographs may differ slightly from the color values cited in the detailed botanical description which accurately describe the actual colors of the new *Schlumbergera* plant.

The photograph on the first sheet comprises a side perspective view of a typical flowering plant of 'Thorsophia' grown in a container.

The photograph on the second sheet are close-up views of a typical flower bud and a typical flower of 'Thorsophia'.

DETAILED BOTANICAL DESCRIPTION

The aforementioned photographs and following observations, measurements and values describe plants grown during the early autumn in 9-cm containers in a glass-covered greenhouse in Odense, Denmark and under cultural practices typical of *Schlumbergera* commercial production. During the production of the plants, day temperatures ranged from 18° C. to 22° C., night temperatures ranged from 16° C. to 20° C. and light levels averaged 30 klux. Plants were pinched one time and were ten months old when the photographs and description were taken. In the following description, color references are made to The Royal Horticultural Society Colour Chart, 2015 Edition, except where general terms of ordinary dictionary significance are used.

Botanical classification: *Schlumbergera hybrida* 'Thorsophia'.

Parentage:

*Female, or seed, parent*.—Proprietary selection of *Schlumbergera hybrida* identified as code number 2010-7.

*Male, or pollen, parent*.—Proprietary selection of *Schlumbergera hybrida* identified as code number 2010-3.

Propagation:

*Type*.—By vegetative cuttings.

*Time to initiate roots, summer*.—About three weeks at temperatures ranging from 22° C. to 24° C.

*Time to initiate roots, winter*.—About three weeks at temperatures ranging from 18° C. to 20° C.

*Time to produce a rooted young plant, summer*.—About 140 days at temperatures ranging from 22° C. to 24° C.

*Time to produce a rooted young plant, winter*.—About 140 days at temperatures ranging from 18° C. to 20° C.

*Root description*.—Fine, fibrous; typically white in color, actual color of the roots is dependent on substrate composition, water quality, fertilizers, substrate temperature and physiological age of roots.

*Rooting habit*.—Moderately freely branching; medium density.

Plant description:

*Plant and growth habit*.—Upright to broadly spreading plant habit; moderately vigorous growth habit.

*Plant height, soil level to top of foliar plane*.—About 12.9 cm.

*Plant height, soil level to top of floral plane*.—About 17.3 cm.

*Plant diameter (spread)*.—About 18.9 cm.

*Lateral stem description*.—Stems are flattened phylloclades with thin joints. Branching habit: Freely branching habit with about nine lateral branches developing per plant; pinching enhances lateral branch development. Phylloclade length: About 4.2 cm. Diameter: About 3.5 cm; at the joint, about 5 mm. Shape: Broadly oblong. Margins: Sharply two-dentate; at the joints, marginal areolas with short bristles, about 1 mm to 3 mm in length and close to 162C to 162D in color. Strength: Moderately strong. Aspect: Upright to perpendicular. Texture and luster: Smooth, glabrous; moderately glossy. Color, developing: Slightly darker than between 143A and 146A. Color, developed: Close to 147A; main vein, close to 143B to 143C, at segment joints, main vein is slightly darker than 143A.

Flower description:

*Flower type and flowering habit*.—Single zygomorphic flowers with numerous perianth segments; flowers face upright to slightly drooping; freely flowering habit with about seven flowers per plant at one time.

*Natural flowering season*.—Plants flower continuously from spring into the autumn in Denmark.

*Flower longevity on the plant*.—About two to three weeks; flowers not persistent.

*Fragrance*.—None detected.

*Flower buds*.—Length: About 1.7 cm. Diameter: About 7 mm. Shape: Ovate to elliptic. Texture and luster: Smooth, glabrous; slightly glossy. Color: Close to 165B to 165D; towards the apex, tinged with close to 65B to 65C.

*Flowers*.—Appearance: Perianth segments fused towards the base giving an elongated tubular appearance to the flowers; flowers sessile. Diameter: About 5 cm by 5.7 cm. Depth (length): About 6.8 cm. Throat diameter: About 7 mm. Tube length: About 3.2 cm. Tube diameter: About 7 mm.

*Perianth segments*.—Quantity and arrangement: About 20 perianth segments arranged in about five whorls; lower 55% portion of the perianth segments are fused. Perianth segment length: About 3.2 cm; varying between 0.3 cm and 6 cm depending on position. Perianth segment width: About 8 mm; varying between 0.3 cm and 1.3 cm depending on position. Perianth segment shape: Oblanceolate. Perianth segment apex: Acute. Perianth segment margin: Entire. Perianth segment texture and luster, upper and lower surfaces: Smooth, glabrous; velvety; slightly glossy. Perianth segment color: When opening, upper and lower surfaces: Close to 16A to 16B; towards the base, fading to closer to NN155D. Fully opened, upper surface: Close to 16A to 16B (closest to 16B); towards the base, fading to closer to NN155D; venation, similar to lamina colors; yellow color becoming closer to 163D with development. Fully opened, lower surface: Close to 14A to 14C; towards the base, fading to closer to NN155D; venation, similar to lamina colors; yellow color becoming closer to 163D with development.

*Reproductive organs*.—Stamens: Quantity per flower: About 75. Filament length: About 3.5 cm to 4.8 cm. Filament color: Close to NN155D. Anther shape: Narrowly oblong. Anther size: About 0.5 mm by 1 mm. Anther color: Close to 8C. Pollen amount: Moderate. Pollen color: Close to 8D. Pistils: Quantity: Typically one. Pistil length: About 5.9 cm. Style length: About 5.5 cm. Style color: Close to N57A. Stigma diameter: About 2 mm. Stigma shape: Club-shaped. Stigma color: Close to between N66A and 67A. Ovary color: Close to 152D.

*Seeds and fruits*.—Seed and fruit production have not been observed on plants of the new *Schlumbergera*.

Disease & pest resistance: Plants of the new *Schlumbergera* have not been noted to be resistant to pathogens and pests common to *Schlumbergera* plants.

Temperature tolerance: Plants of the new *Schlumbergera* have been observed to tolerate high temperatures of about 40° C. and to be suitable for USDA Hardiness Zones 10 to 13.

It is claimed:

1. A new and distinct *Schlumbergera* plant named 'Thorsophia' as illustrated and described.

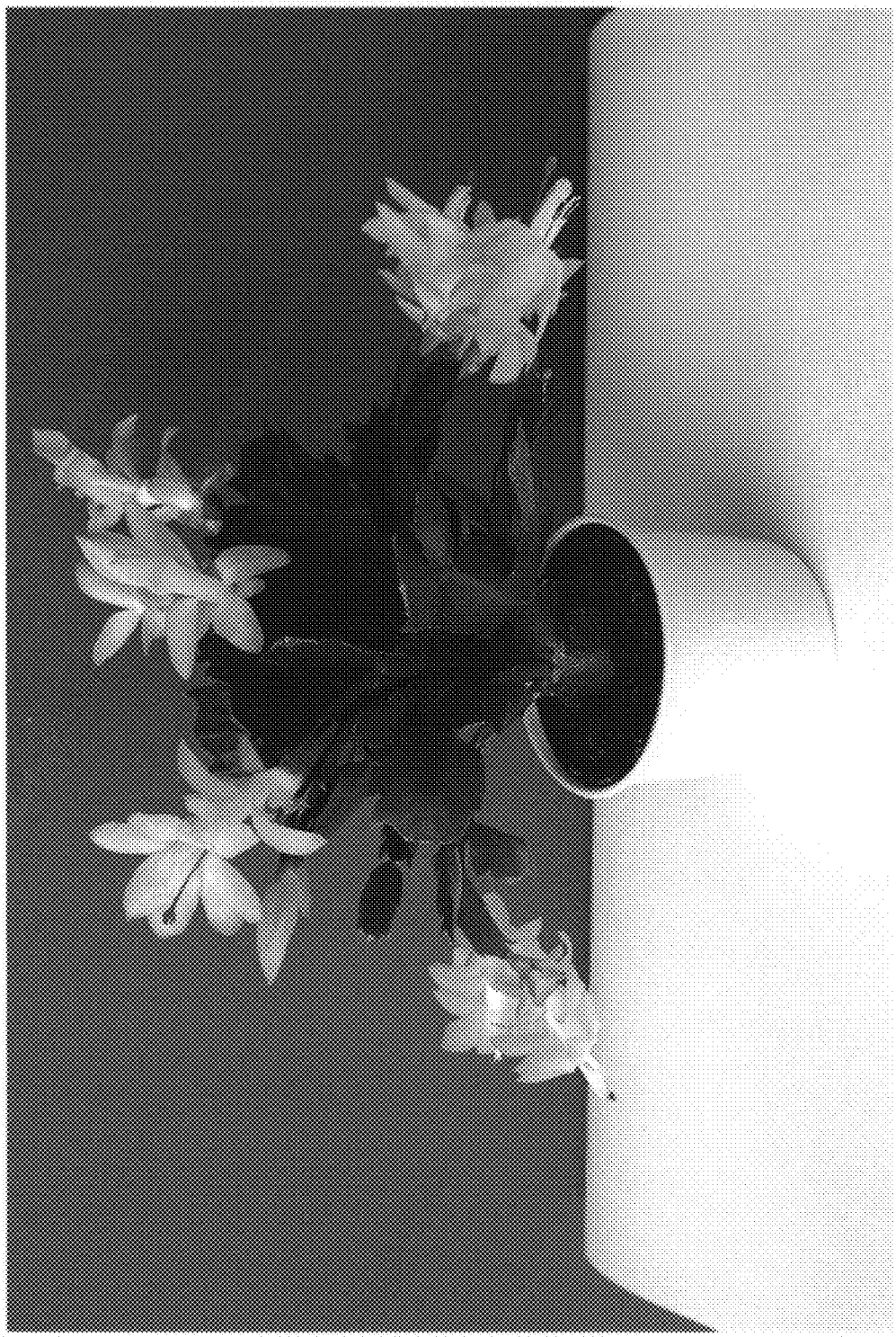

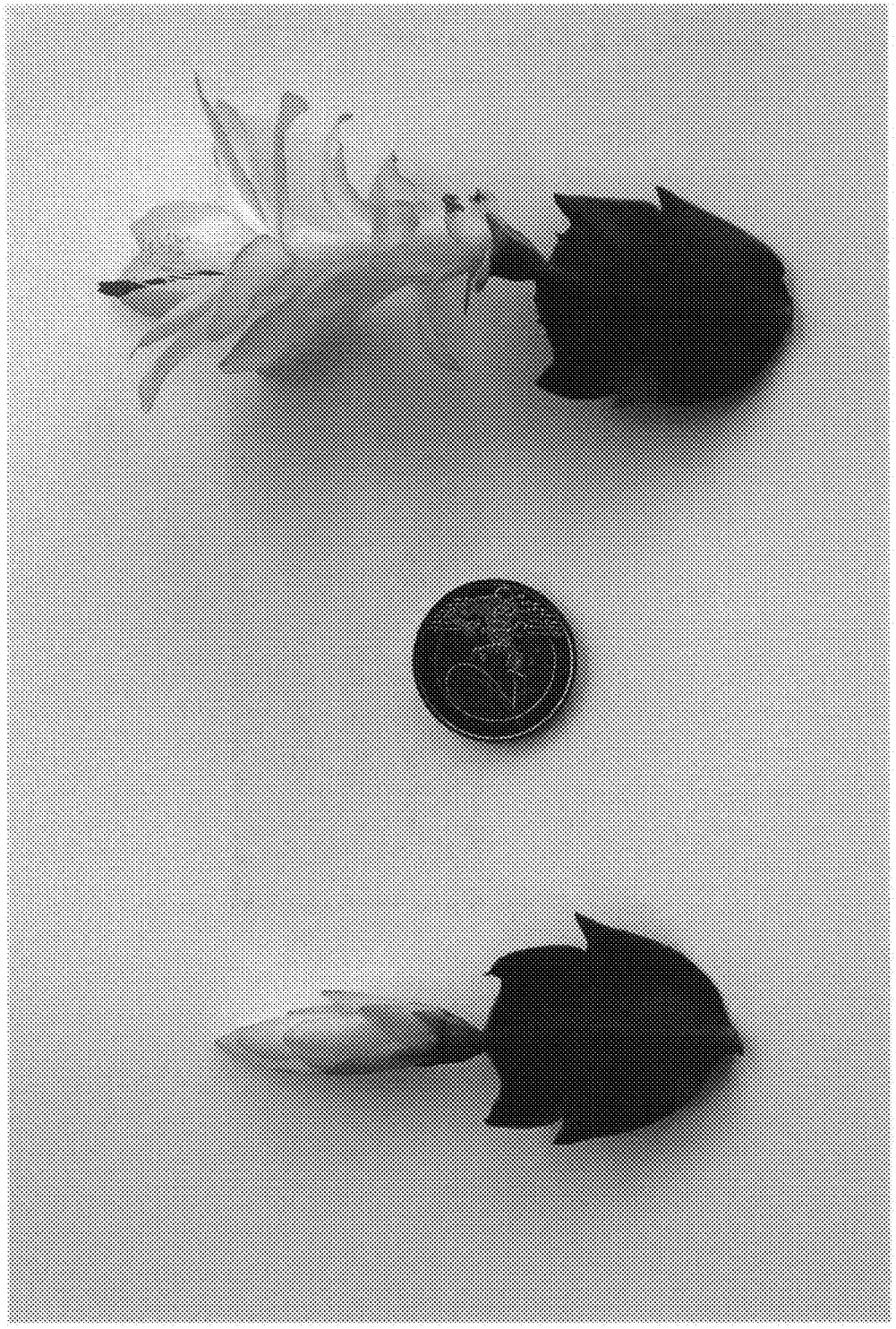

* * * * *